(12) United States Patent
Watanabe et al.

(10) Patent No.: US 12,738,369 B2
(45) Date of Patent: Sep. 15, 2026

(54) MEDICAL IMAGE DIAGNOSTIC APPARATUS AND STORAGE MEDIUM

(71) Applicant: Canon Kabushiki Kaisha, Tokyo (JP)

(72) Inventors: Yoshiteru Watanabe, Nasushiobara (JP); Shinya Ozawa, Saitama (JP); Takeshi Ishimoto, Arakawa (JP)

(73) Assignee: Canon Kabushiki Kaisha, Tokyo (JP)

( * ) Notice: Subject to any disclaimer, the term of this patent is extended or adjusted under 35 U.S.C. 154(b) by 200 days.

(21) Appl. No.: 18/413,830

(22) Filed: Jan. 16, 2024

(65) Prior Publication Data

US 2024/0249832 A1 Jul. 25, 2024

(30) Foreign Application Priority Data

Jan. 19, 2023 (JP) ................................ 2023-006543

(51) Int. Cl.
*G16H 40/40* (2018.01)
*A61B 5/055* (2006.01)
*G16H 70/20* (2018.01)

(52) U.S. Cl.
CPC ............. *G16H 40/40* (2018.01); *A61B 5/055* (2013.01); *G16H 70/20* (2018.01)

(58) Field of Classification Search
CPC ...... G01R 33/28; G01R 33/288; G01R 33/32; G01R 33/34; G01R 33/34015; G01R 33/34023; G01R 33/3403; G01R 33/34038; G01R 33/34046; G01R 33/34053; G01R 33/34061; G01R 33/34069; G01R 33/34076
See application file for complete search history.

(56) References Cited

U.S. PATENT DOCUMENTS

2018/0365025 A1* 12/2018 Almecija .............. G06F 3/0482
2023/0187087 A1* 6/2023 Chamarthi ............. G16H 30/20 705/2

FOREIGN PATENT DOCUMENTS

JP 2004-147899 A 5/2004

* cited by examiner

*Primary Examiner* — Tung X Nguyen
(74) *Attorney, Agent, or Firm* — Oblon, McClelland, Maier & Neustadt, L.L.P.

(57) ABSTRACT

A medical image diagnostic apparatus of an embodiment includes processing circuitry. The processing circuitry acquires skill information regarding a skill of a user who sets the medical image diagnostic apparatus. The processing circuitry provides setting information for the medical image diagnostic apparatus according to the skill of the user based on the acquired skill information to the user.

12 Claims, 8 Drawing Sheets

FIG. 4

TECHNICIAN NAME: ○○3

TECHNICIAN NAME: ○○2

TECHNICIAN NAME: ○○1

| | GUIDANCE DISPLAY | | | SETTING REVIEW | REMARKS |
|---|---|---|---|---|---|
| | (DETAILED) | (NORMAL) | (OUTLINE) | | |
| ROUTINE EXAMINATION | | | | | INDIVIDUAL EXAMINATION POSSIBLE |
| ELECTROCARDIOGRAM GATED EXAMINATION | ✓ | | | | INDIVIDUAL EXAMINATION POSSIBLE WITH GUIDANCE DISPLAY |
| RESPIRATORY GATED EXAMINATION | | | | | INDIVIDUAL EXAMINATION POSSIBLE |
| MSK EXAMINATION | | ✓ | | ✓ | GUIDANCE DISPLAY SETTING REVIEW REQUIRED |
| INFREQUENTLY USED COIL EXAMINATION | ✓ | | | ✓ | |
| CONTRAST EXAMINATION | | | ✓ | | |
| VERTEBRAL CURVATURE | | | | ✓ | EXAMINATION ORDER CHECK WITH CEILING CAMERA |
| COIL/BODY POSITION CHANGE | | | | ✓ | USUAL RESPONSE IMPOSSIBLE |

SKILL LEVEL:3

SKILL LEVEL:2

SKILL LEVEL:1

| | GUIDANCE DISPLAY | | | SETTING REVIEW | REMARKS |
|---|---|---|---|---|---|
| | (DETAILED) | (NORMAL) | (OUTLINE) | | |
| ROUTINE EXAMINATION | | | ✓ | | |
| ELECTROCARDIOGRAM GATED EXAMINATION | ✓ | | | | |
| RESPIRATORY GATED EXAMINATION | | ✓ | | | |
| MSK EXAMINATION | ✓ | | | ✓ | |
| INFREQUENTLY USED COIL EXAMINATION | ✓ | | | ✓ | |
| CONTRAST EXAMINATION | | ✓ | | | |
| VERTEBRAL CURVATURE | | | | ✓ | |
| COIL/BODY POSITION CHANGE | | | | ✓ | |

MEDICAL IMAGE DIAGNOSTIC APPARATUS AND STORAGE MEDIUM

CROSS-REFERENCE TO RELATED APPLICATION

The present application claims priority based on Japanese Patent Application No. 2023-006543, filed Jan. 19, 2023, the content of which is incorporated herein by reference.

FIELD

Embodiments disclosed in this specification and the drawings relate to a medical image diagnostic apparatus and a storage medium.

BACKGROUND

Conventionally, a magnetic resonance imaging (MRI) apparatus (hereinafter referred to as an MRI apparatus) has been used as a medical diagnostic apparatus for performing diagnosis using images. In an MRI apparatus, at the time of starting a diagnosis of a patient (hereinafter referred to as a subject), a setting operation of setting the subject such that an imaging unit is at the center of the magnetic field, appropriately disposing a reception coil at an imaging region, adjusting the body position of subject, and the like is required in order to curb the influence of magnetic field distortion.

At the time of disposing the reception coil as a setting operation, for example, it is required to stop the tape at an appropriate position at the time of winding the coil, route a cable such that it does not interfere with imaging, and the like. In adjusting the body position of a subject, for example, when imaging one leg of the subject, it is required that the leg on the opposite side be placed in a position where it is unlikely to interfere with imaging. For this reason, the setting operation cannot be performed easily.

Since the setting operation is performed by, for example, a technician, support using guidance or the like can be provided when a less skilled technician performs the setting operation, for example. However, since the skill level in setting is not uniform and differs from technician to technician, it is difficult for experienced technicians to provide support with appropriate guidance and advice, for example.

For example, if a technician has some experience, he or she can perform the setting operation while viewing a manual. In this case, there is no need for support from a skilled technician if it is a normal setting operation, for example, but if setting is difficult or the technician is confused about what to do, he or she may want to get advice from a skilled technician.

BRIEF DESCRIPTION OF THE DRAWINGS

FIG. 4 is a diagram showing an example of a guidance designation table.

FIG. 5 is a diagram showing another example of a guidance designation table.

DETAILED DESCRIPTION

Hereinafter, a medical image diagnostic apparatus and a storage medium of an embodiment will be described with reference to the drawings.

A medical image diagnostic apparatus of an embodiment includes processing circuitry. The processing circuitry acquires skill information regarding a skill of a user who sets the medical image diagnostic apparatus. The processing circuitry provides setting information for the medical image diagnostic apparatus according to the skill of the user based on the acquired skill information to the user. Accordingly, it is possible to perform appropriate support for the user.

The medical image diagnostic apparatus of the embodiment is, for example, an MRI apparatus 200. The MRI apparatus 200 is a medical diagnostic apparatus that radiates RF pulses to a subject (for example, a human body) while applying a strong magnetic field, receives electromagnetic waves generated from hydrogen nuclei in the body of the subject due to the nuclear magnetic resonance phenomenon through an RF coil, and captures a tomographic image (hereinafter referred to as an "MR images") of the subject by reconstructing the image from nuclear magnetic resonance signals (hereinafter referred to as "MR signals") based on the received electromagnetic waves. In the embodiment, the medical image diagnostic apparatus is the MRI apparatus 200, but the medical image diagnostic apparatus may be other than the MRI apparatus 200. The medical image diagnostic apparatus may be, for example, an X-ray computed tomography apparatus, an X-ray diagnostic apparatus, an ultrasound diagnostic apparatus, a nuclear medicine diagnostic apparatus, or the like.

The MRI apparatus may capture an MR image of a subject by reconstructing an MR signal based on electromagnetic waves received through an RF coil attached to the subject. By displaying an MR image of a subject, the MRI apparatus allows a person who performs an MRI examination (such as a doctor or a technician) to visually check whether or not the subject has a lesion.

Figure 1:
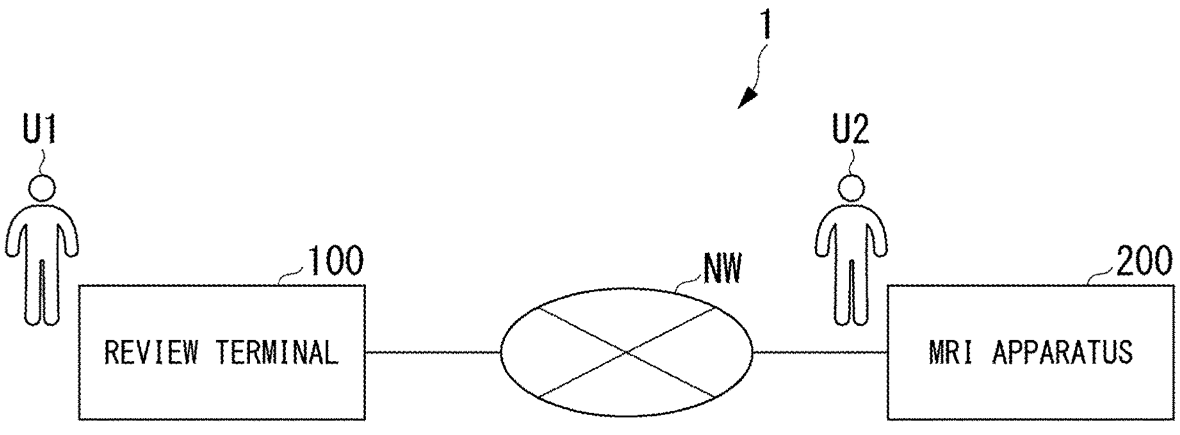
FIG. 1 is a block diagram showing an example of a configuration of a medical image diagnostic system of an embodiment.

FIG. 1 is a block diagram showing an example of a configuration of a medical image diagnostic system 1 of an embodiment. The medical image diagnostic system 1 of the embodiment includes, for example, a review terminal 100 and an MRI apparatus 200. The review terminal 100 and the MRI apparatus 200 are capable of communicating with each other via a network NW.

The review terminal 100 is operated by, for example, a first technician U1. In the MRI apparatus 200, a second technician U2 other than the first technician U1 sets the MRI apparatus 200 when performing image diagnosis. The first technician U1 is, for example, a skilled technician who is good at setting the MRI apparatus 200. The second technician U2 is a variety of technicians, and technicians have different skill levels in setting. The first technician U1 performs a review together with the second technician U2 and gives advice to the second technician U2 when the second technician U2 sets the MRI apparatus 200. As a plurality of users in the embodiment, the first technician U1 is an example of another user, and the second technician U2 is an example of a user.

Figure 2:
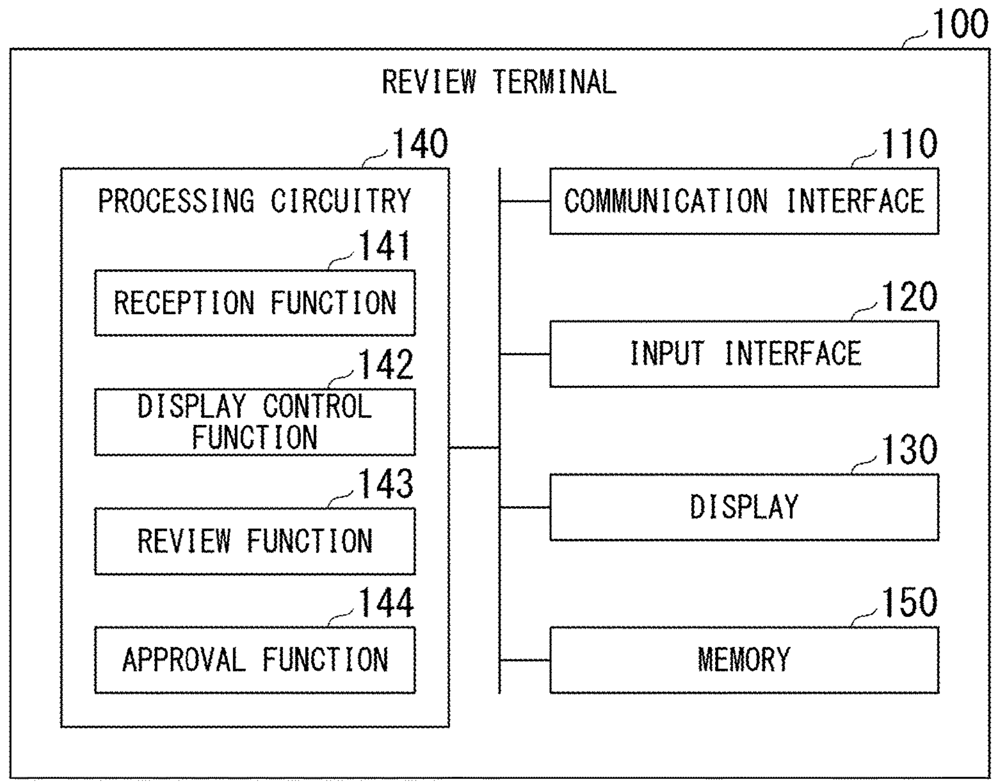
FIG. 2 is a block diagram showing an example of a configuration of a review terminal of an embodiment.

FIG. 2 is a block diagram showing an example of a configuration of the review terminal 100 of the embodiment. The review terminal 100 includes, for example, a communication interface 110, an input interface 120, a display 130, processing circuitry 140, and a memory 150. The review terminal 100 is installed at, for example, a location away from the MRI apparatus 200. The review terminal 100 may be disposed near the MRI apparatus 200.

The communication interface 110 communicates with an external device such as the MRI apparatus 200 via a network NW such as a local area network (LAN), for example. The communication interface 110 receives various types of information transmitted from external devices and outputs the information to the processing circuitry 140. The communication interface 110 transmits various types of information generated by the processing circuitry 140 to external devices.

The communication interface 110 includes, for example, a communication interface such as a network interface card (NIC). The network NW may include the Internet, a cellular network, a Wi-Fi network, a wide area network (WAN), and the like instead of or in addition to a LAN.

The input interface 120 receives various input operations from the first technician U1 and the like, converts the received input operations into electrical signals, and outputs the electrical signals to the processing circuitry 140. For example, in a case where an input operation is performed by a user, the input interface 120 generates input operation information according to the input operation. The input operation information includes, for example, advice given by the first technician U1 to the second technician U2 regarding settings. The input interface 120 outputs the generated input operation information corresponding to the input operation to the processing circuitry 140.

The display 130 displays various types of information. For example, the display 130 displays an image generated by the processing circuitry 140, a graphical user interface (GUI) for receiving various input operations from an operator, and the like. For example, the display 130 is a liquid crystal display (LCD), a cathode ray tube (CRT) display, an organic electroluminescence (EL) display, or the like.

The processing circuitry 140 includes, for example, a reception function 141, a display control function 142, a review function 143, and an approval function 144. The processing circuitry 140 realizes these functions by, for example, a hardware processor (computer) executing a program stored in the memory (storage circuit) 150. The memory 150 is realized by, for example, a semiconductor memory such as a ROM, a RAM, or a flash memory, a hard disk drive (HDD), an optical disc, or the like.

The reception function 141 in the processing circuitry 140 receives various types of information transmitted from an external device such as the MRI apparatus 200 and received through the communication interface 110. The reception function 141 receives information such as a review request and an approval request transmitted by the MRI apparatus 200, a video captured by an optical camera 61 provided in the MRI apparatus 200, and the vocal sound of the second technician U2, for example. Instead of or in addition to a video captured by the optical camera 61, a video captured by the optical camera 61 may be used.

The display control function 142 controls content displayed on the display 130. The display control function 142 causes the display 130 to display a video according to information received by the reception function 141, for example. The display control function 142 causes the display 130 to display input operation information output by the input interface 120, for example.

In a case where the reception function 141 receives a review request output from the communication interface 110, the review function 143 notifies the first technician U1 that a review request has been made by displaying the request on the display 130, or the like. The first technician U1 receives the notification from the review function 143, executes a review with the second technician U2, and performs an input operation on the input interface 120 according to the content of the advice given to the second technician U2.

While the first technician U1 executes a review with the second technician, the review function 143 provides information such as a video captured by the optical camera 61 (hereinafter referred to as a review video) and the vocal sound of the second technician U2 (hereinafter referred to as a review vocal sound). For example, the review function 143 causes the review video to be displayed on the display 130 and causes the review vocal sound to be output through a speaker or a headset worn by the first technician U1. The first technician U1 performs an input operation on the input interface 120 according to advice given to the second technician U2 while viewing the review video and listening to the review vocal sound.

The review function 143 generates advice information according to input operation information output by the input interface 120. The advice information includes verbal information and video information (including image information) using drawings, images, videos, and the like. The review function 143 transmits the generated advice information to the MRI apparatus 200 using the communication interface 110 and causes the display 130 to display the advice information using the display control function 142. The advice information is proposed by the first technician U1 different from the second technician U2. The advice information is an example of setting information.

In a case where the reception function 141 has received an approval request output by the communication interface 110, the approval function 144 notifies the first technician U1 that a setting approval request has been made by displaying it on the display 130, or the like. The first technician U1 receives the notification from the approval function 144, determines whether setting can be approved, and performs an input operation on the input interface 120 according to the determination result.

The approval function 144 generates approval information in a case where the input operation information output by the input interface 120 indicates that setting can be approved. The approval function 144 transmits the generated approval information to the MRI apparatus 200 using uses communication interface 110 and causes the display 130 to display the approval information using the display control function 142.

Figure 3:
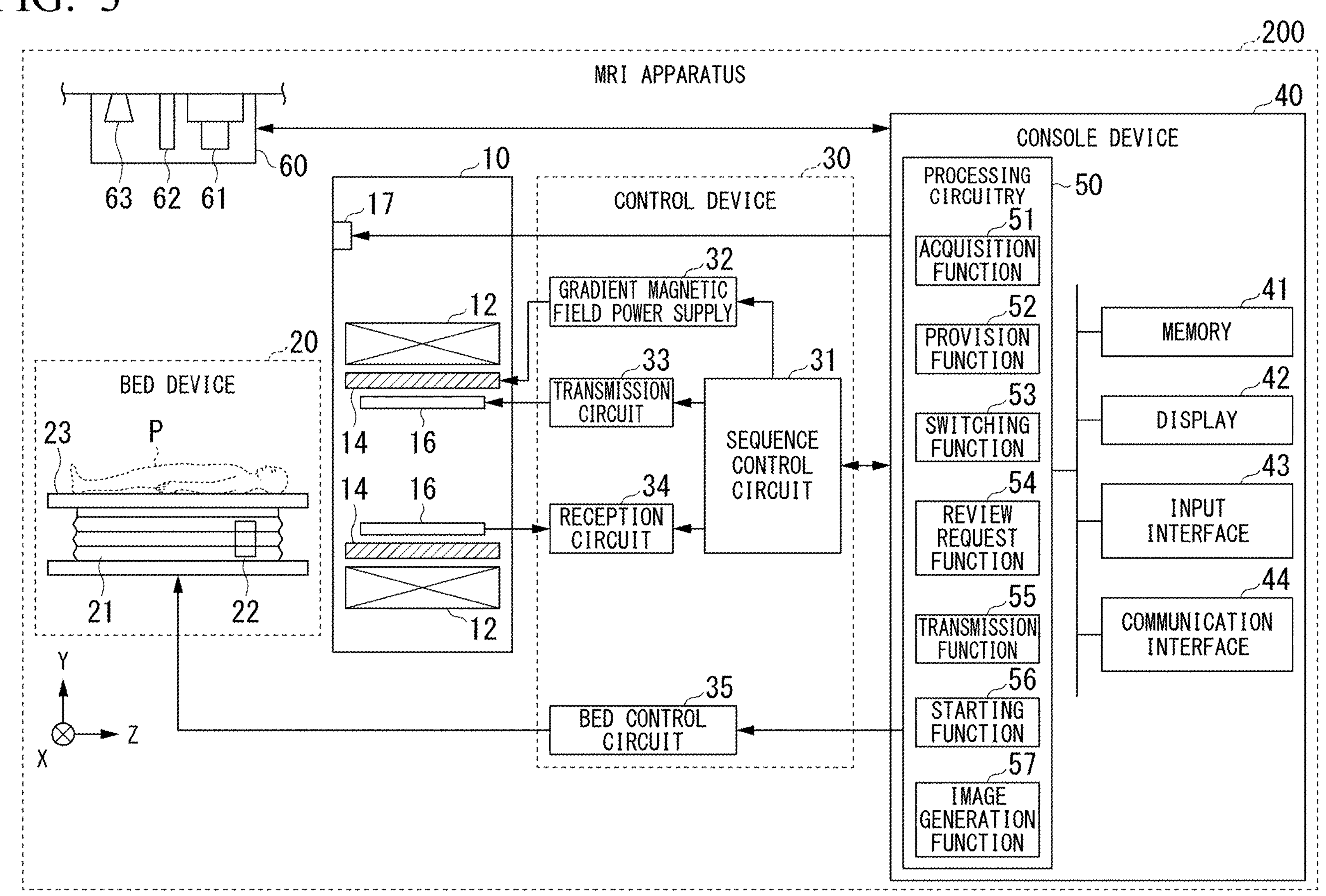
FIG. 3 is a block diagram showing an example of a configuration of an MRI apparatus of an embodiment.

FIG. 3 is a block diagram showing an example of a configuration of the MRI apparatus 200 of the embodiment. The MRI apparatus 200 includes, for example, a gantry device 10, a bed device 20, a control device 30, a console device 40, and accessory equipment 60. The accessory equipment 60 includes, for example, the optical camera 61, a microphone 62, and a speaker 63. Although the control device 30 and the console device 40 are described as being separate from the gantry device 10 in the present embodiment, some or all of components of the control device 30 and the console device 40 may be included in the gantry device 10.

The gantry device 10 includes, for example, a static magnetic field magnet 12, a gradient magnetic field coil 14, and an RF coil 16. The static magnetic field magnet 12 is a magnet formed in a substantially cylindrical hollow form. The static magnetic field magnet 12 generates a uniform static magnetic field in the internal space. The static magnetic field magnet 12 is, for example, a permanent magnet, a superconducting magnet, or the like. In a case where the static magnetic field magnet 12 is a superconducting magnet, it receives power supply from a static magnetic field power source that is not shown and generates a static magnetic field.

The gradient magnetic field coil 14 is a coil formed in a substantially cylindrical hollow form. The gradient magnetic field coil 14 is disposed inside the static magnetic field magnet 12. The gradient magnetic field coil 14 is formed by combining three coils corresponding to an X axis, a Y axis, and a Z axis, which are orthogonal to each other. The three coils corresponding to the directions of the respective axes individually receive current supply from the gradient magnetic field power supply 32 and generate gradient magnetic fields having magnetic field strengths changing along the X axis, the Y axis, and the Z axis within an imaging space (magnetic field space) of the MRI apparatus 200 into which a subject P has been introduced.

The RF coil 16 is a whole-body coil that is housed within the gantry device 10 and is configured to surround the subject P within the imaging space. The RF coil 16 receives RF pulses from a transmission circuit 33 and generates high frequency magnetic fields. The RF coil 16 receives an MR signal emitted from the subject P according to the influence of the high frequency magnetic fields. Upon receiving the MR signal, the RF coil 16 outputs the received MR signal to a reception circuit 34.

The bed device 20 is a device that places the subject P to be imaged thereon and moves the subject P into the inside of the gantry device 10 (inside a cavity of the static magnetic field magnet 12, gradient magnetic field coil 14, and RF coil 16, that is, inside an imaging port). The bed device 20 includes, for example, a base 21, a bed driving device 22, and a top plate 23. The base 21 includes a housing that supports a support frame that supports the top plate 23 such that the support frame is movable in the vertical direction (Y-axis direction). The bed driving device 22 includes a motor and an actuator. The bed driving device 22 moves the top plate 23 in the longitudinal direction (Z-axis direction) along the support frame. Further, the bed driving device 22 moves the top plate 23 in the vertical direction (Y-axis direction). The top plate 23 is a plate-shaped member on which the subject P is placed.

The control device 30 controls operations of the gantry device 10 and the bed device 20 according to control from the console device 40. The control device 30 includes, for example, a sequence control circuit 31, a gradient magnetic field power supply 32, the transmission circuit 33, the reception circuit 34, and a bed control circuit 35. The control device 30 may be provided within the gantry device 10 or may be provided within the console device 40.

The sequence control circuit 31 is a sequencer that performs imaging of the subject P by driving the gradient magnetic field power supply 32, the transmission circuit 33, and the reception circuit 34 on the basis of sequence information set by the console device 40. The sequence control circuit 31 may be, for example, processing circuitry including a processor such as a CPU. The sequence information is, for example, information in which a procedure for performing imaging processing for imaging the subject P in the MRI apparatus 200 is defined in advance.

The gradient magnetic field power supply 32 individually supplies current to each of the three coils corresponding to the direction of each axis in the gradient magnetic field coil 14.

The transmission circuit 33 supplies RF pulses to the RF coil 16. The RF pulses supplied by the transmission circuit 33 to the RF coil 16 are pulses corresponding to the Larmor frequency which is determined by the type of a target atomic nucleus and the strength of a magnetic field.

The reception circuit 34 detects an MR signal output by the RF coil 16 and generates MR data representing the detected MR signal. The reception circuit 34 generates the MR data by converting the MR signal into digital data, for example. The reception circuit 34 outputs the generated MR data to the sequence control circuit 31. The sequence control circuit 31 transfers the MR data output by the receiving circuit 34 to the console device 40.

The bed control circuit 35 outputs a drive control signal for driving the bed driving device 22 to the bed driving device 22 according to control from the console device 40. The bed control circuit 35 may be provided within the gantry device 10 or may be provided within the bed device 20. In this case, the bed control circuit 35 outputs a control signal according to an input signal that is input from an input interface, which is not shown, included in the device in which the bed control circuit 35 is provided, when an operator such as the second technician U2 operates the input interface which is not shown to a bed driving device, which is not shown, included in the bed device 20.

The console device 40 controls the entire MRI apparatus 200 and collects MR data. The console device 40 includes, for example, a memory 41, a display 42, an input interface 43, a communication interface 44, and processing circuitry 50.

The memory 41 is realized by, for example, a semiconductor memory element such as a ROM, a RAM, or a flash memory, a hard disk drive (HDD), an optical disk, or the like. The memory 41 stores data such as MR data output by the sequence control circuit 31 and a reconstructed image (MR image) generated on the basis of the MR data, for example.

The memory 41 stores a guidance designation table. The guidance designation table is a table for designating guidance to be displayed on the display 42 when the second technician U2 sets the MRI apparatus 200. FIG. 4 is a diagram showing an example of the guidance designation table.

The guidance designation table is set for each technician depending on the technician's skill, for example. Since skill differs from technician to technician, a plurality of guidance designation tables are set depending on the level of the technician's skill. The guidance designation table includes the name of a technician. By designating the name of a technician, a guidance designation table corresponding to the technician is designated. The name of a technician is an example of skill information regarding a technician's skill.

The guidance designation table shows the content of guidance to be displayed on the display 42 according to the type of examination. In the guidance designation table shown in FIG. 4, the content of guidance is set for each technician. The content of guidance is an example of setting information.

The content of guidance may be displayed on the display 42 or may be conveyed to the second technician U2 by a vocal sound. In a case where the content of guidance is transferred to the second technician U2 by the vocal sound, the vocal sound may be output from a speaker, or the vocal sound may be output using earphones to prevent the subject P from hearing the content of guidance. For example, three types of guidance content of "detailed," "normal," and "outline" are provided for content of each examination. Guidance is set depending on a use form of the MRI apparatus 200. The content of examination is an example of a use form of the MRI apparatus 200.

The guidance "detailed" shows the content of setting in detail. For example, in the guidance "detailed," the content of setting is explained such that it is easily ascertained using videos, images, and explanatory text. For this reason, the explanation time for the guidance "detailed" is set to be long. The guidance "detailed" is mainly used by technicians with low setting skills.

The guidance "normal" shows the content of setting to a degree to which it is not excessively detailed. For example, in the guidance "normal," the content of setting processing is explained in a manner that is ascertained to some extent using images and explanatory text. The explanation time for the guidance "normal" is set to be moderate. The guidance "normal" is guidance mainly used by technicians with ordinary setting skills.

The guidance "outline" shows an outline of setting. For example, in the guidance "outline," setting is briefly explained using images and explanatory text. The explanation time for the guidance "outline" is set to be short. The guidance "outline" is, for example, guidance used by technicians with high setting skills.

For example, the second technician U2 whose name (technician name) is "OO1" has low skill in "electrocardiogram gated examination" and high skill in "contrast examination." Therefore, in the case of the second technician U2 whose technician name is "OO1," guidance is not designated for "routine examination" and "respiratory gated examination," and the guidance "detailed" is designated for "electrocardiogram gated examination" and "infrequently used coil examination." The guidance "normal" is designated for an MSK examination, and the guidance "outline" is designated for a contrast examination.

In addition to guidance display, setting processing requires advice from a skilled first technician U1 or the like in most cases in the "MSK examination" and the "infrequently used coil test." For this reason, in the "MSK examination" and the "infrequently used coil test," a setting review by the first technician U1 is predefined.

In addition, if there is a "vertebral curvature," "change in the installation state of the coil," or "change in the body position" of the subject P, guidance corresponding thereto is not displayed, but a setting review by the second technician U2 will be required. The "infrequently used coil examination" is an examination that uses a coil that is infrequently used. The "MSK examination" is a musculoskeletal test.

In the embodiment, the guidance designation table is set for each technician, but the guidance designation table may be set in other ways. For example, a plurality of guidance designation tables may be set on the basis of the skill level of a technician. A skill level is an example of skill. FIG. 5 is a diagram showing another example of the guidance designation table.

A guidance designation table that is set on the basis of the skill level of a technician is set for each of a plurality of levels depending on skill, for example, each of technician's skill levels 1, 2, 3, . . . . For example, the higher a numerical value indicated by a skill level, the lower the skill level, and for example, skill level 1 is set as the lowest skill level. An appropriate number of skill levels is set. In this manner, the guidance designation table may be set depending on the skill level of a technician.

Referring back to FIG. 3, the display 42 displays various types of information. For example, the display 42 displays images generated by the processing circuitry 50, a graphical user interface (GUI) images through which various operations performed by the operator of the MRI apparatus 200 are received, and the like. The display 42 is, for example, a liquid crystal display (LCD), a CRT (cathode ray tube) display, an organic EL (electroluminescence) display, or the like.

The display 42 may be provided on the gantry device 10, for example. The display 42 may be of a desktop type, or may be a display device (for example, a tablet terminal) that can wirelessly communicate with the main body of the console device 40. The display 42 may be provided at a location away from the gantry device 10 in an examination room, and for example, may be provided on a wagon disposed on the side of the gantry device 10 during setting or may be hung from the ceiling of the examination room.

The input interface 43 receives various input operations performed by the operator of the MRI apparatus 200 and outputs electrical signals indicating the content of the received input operations to the processing circuitry 50. The input interface 43 receives, for example, operations of inputting second technician information regarding the second technician U2 who performs an examination using the MRI apparatus 200, examination content information indicating the content of the examination, a review request, a switching request, and an approval request by the second technician U2. The second technician information is information for identifying the second technician U2 and includes, for example, information on the name of the second technician U2. The input interface 43 outputs information corresponding to the received input operations to the processing circuitry 50.

The input interface 43 is realized by, for example, a mouse, a keyboard, a touch panel, a trackball, a switch, a button, a joystick, a camera, an infrared sensor, a microphone, or the like. In a case where the input interface 43 is a touch panel, the display 42 may be formed integrally with the input interface 43. The input interface 43 may be provided in the gantry device 10. The input interface 43 may be realized by a display device (for example, a tablet terminal) that can wirelessly communicate with the main body of the console device 40.

In this specification, the input interface 43 is not limited to those that include physical operation components such as the mouse and keyboard described above. For example, electric signal processing circuitry that receives an electric signal corresponding to an input operation from external input equipment provided separately from the console device 40 and outputs this electric signal to the processing circuitry 50 is also included in examples of the input interface 43.

The communication interface 44 communicates with an external device such as the review terminal 100 via a network NW such as a LAN, for example. The communication interface 44 receives various types of information such as advice information transmitted from an external device such as the review terminal 100, for example. The communication interface 44 outputs the received information to the processing circuitry 50. The communication interface 44 includes, for example, a communication interface such as an NIC.

The processing circuitry 50 communicates with external devices and controls the overall operation of the MRI apparatus 200. The processing circuitry 50 sets sequence information in the sequence control circuit 31. The processing circuitry 50 includes, for example, an acquisition function 51, a provision function 52, a switching function 53, a review request function 54, a transmission function 55, a starting function 56, and an image generation function 57. The processing circuitry 50 realizes these functions by, for example, a hardware processor (computer) executing a program stored in the memory (storage circuit) 41.

A hardware processor is, for example, circuitry such as a CPU, a graphics processing unit (GPU), an application specific integrated circuit (ASIC), a programmable logic device (for example, a simple programmable logic device (SPLD) or a complex programmable logic device (CPLD)), or a field programmable gate array (FPGA)).

Instead of storing the program in the memory 41, the program may be directly incorporated into the circuit of the hardware processor. In this case, the hardware processor realizes the functions by reading and executing the program incorporated into the circuit. The aforementioned program may be stored in advance in the memory 41, or may be stored in a non-transitory storage medium such as a DVD or a CD-ROM and installed in the memory 41 from the non-transitory storage medium when the non-transitory storage medium is set in a drive device (not shown) of the console device 40.

The hardware processor is not limited to being configured as a single circuit and may be configured as a single hardware processor by combining a plurality of independent circuits to realize each function. Further, a plurality of components may be integrated into one hardware processor to realize each function.

The acquisition function 51 acquires information corresponding to an input operation received by the input interface 43, advice information outputted by the communication interface 44, and the like. The acquisition function 51 acquires, for example, second technician information, examination content information, a switching request, a review request, an approval request, approval information, and the like.

The acquisition function 51 further acquires MR data transferred by the sequence control circuit 31 in order to generate a medical image (MR image). The MR data is obtained by converting an MR signal into digital data by the reception circuit 34. The acquisition function 51 stores the acquired MR data in the memory 41. The acquisition function 51 is an example of an acquisition unit.

The provision function 52 reads, from the memory 41, a guidance designation table corresponding to the name of a second technician U2 included in the second technician information acquired by the acquisition function 51. The provision function 52 checks the content of an examination on the basis of the examination content information acquired by the acquisition function 51, and identifies the necessity of guidance and review to be provided with reference to the read guidance designation table. The provision function 52 provides setting information corresponding to any one of a plurality of levels to the second technician U2. The provision function 52 is an example of a provision unit.

The switching function 53 switches the content of guidance provided to the second technician U2 when the acquisition function 51 has acquired a switching request based on an instruction from the second technician U2 outputted by the input interface 43. For example, in a case where a request to switch to the guidance "normal" is output while the guidance "detailed" is being provided, the switching function 53 switches the content of guidance provided to the second technician U2 from the guidance "detailed" to the guidance "normal." The switching function 53 is an example of a switching unit.

In a case where the acquisition function 51 has acquired a review request from the second technician U2 output by the input interface 43, the review request function 54 requests a review for obtaining advice from the first technician U1 who operates the review terminal 100. Therefore, the review request function 54 transmits the acquired review request to the review terminal 100 using the communication interface 44. The review request function 54 is an example of a review request unit.

The transmission function 55 generates status information regarding the status of setting executed in the MRI apparatus 200 in a case where the review request function 54 transmits a review request to the review terminal 100 and the first technician U1 and the second technician U2 start a review. The transmission function 55 transmits the generated status information to the review terminal 100 using the communication interface 44. The status information includes information such as videos captured by the optical camera 61, vocal sounds collected by the microphone 62, and characters input through the input interface 43, for example. The transmission function 55 is an example of a transmission unit.

The transmission function 55 transmits advice information transmitted by the review terminal 100 and received and output by the communication interface 44 to the second technician U2 while a review is executed between the first technician U1 and the second technician U2. For example, the transmission function 55 displays verbal information in words as text on the display 42 or outputs it as a vocal sound using the speaker 63 or the like. The transmission function 55 displays, for example, video information (including image information) using drawings, images, videos, and the like on the display 42.

In a case where the acquisition function 51 has acquired an approval request from the second technician U2 output by the input interface 43, the transmission function 55 requests approval of setting by the first technician U1 operating the review terminal 100. Therefore, the transmission function 55 transmits the approval request acquired by the acquisition function 51 to the review terminal 100 using the communication interface 44.

The transmission function 55 transmits status information to the review terminal 100 even after setting is completed and imaging of the subject P is started. Therefore, even if the first technician U1 is in charge of the imaging operation at the time of imaging the subject P, for example, the status of setting can be transmitted to the first technician U1.

The starting function 56 causes the MRI apparatus 200 to start an operation of performing an examination in a case where the acquisition function 51 has acquired approval information transmitted by the review terminal 100. The starting function 56 executes AutoIn to automatically move the top plate 23 of the bed device 20 into the gantry device 10 in order to cause the MRI apparatus 200 to start an operation of performing an examination.

The image generation function 57 performs predetermined reconstruction processing on the MR data acquired by the acquisition function 51 or the MR data stored in the memory 41 to generate a reconstructed image. The image generation function 57 converts a reconstructed image stored in the memory 41 into a three-dimensional image or a cross-sectional image data of an arbitrary cross section on the basis of an input operation received by the input interface 43 using a known method. The image generation function 57 stores the converted cross-sectional image data in the memory 41 as an MR image.

The optical camera 61 is attached, for example, to the ceiling in the examination room where the MRI apparatus 200 is installed. The optical camera 61 captures an image of the subject P on the top plate 23 of the bed device 20 and the surrounding environment of the subject P. The optical camera 61 transmits the captured image including the subject P and the surrounding environment to the console device 40.

The microphone 62 is provided adjacent to the optical camera 61, for example. The microphone 62 collects sound within the examination room, particularly, the vocal sound of the second technician U2. The microphone 62 transmits the collected sound to the console device 40. The microphone 62 may be provided at a position other than the position adjacent to the optical camera 61. The microphone 62 may be provided on the gantry device 10 or the bed device 20, for example.

The speaker 63 is provided adjacent to the optical camera 61, for example. The speaker 63 outputs the sound transmitted by the console device 40, for example, the sound uttered by the first technician U1. The sound output by the speaker 63 can be heard by the second technician U2 in the examination room, for example. The speaker 63 may be provided at a position other than the position adjacent to the optical camera 61. The speaker 63 may be provided on the gantry device 10 or the bed device 20, for example. Instead of or in addition to the form in which the speaker 63 is provided, a headset worn by the second technician U2 may be provided.

Figure 6:
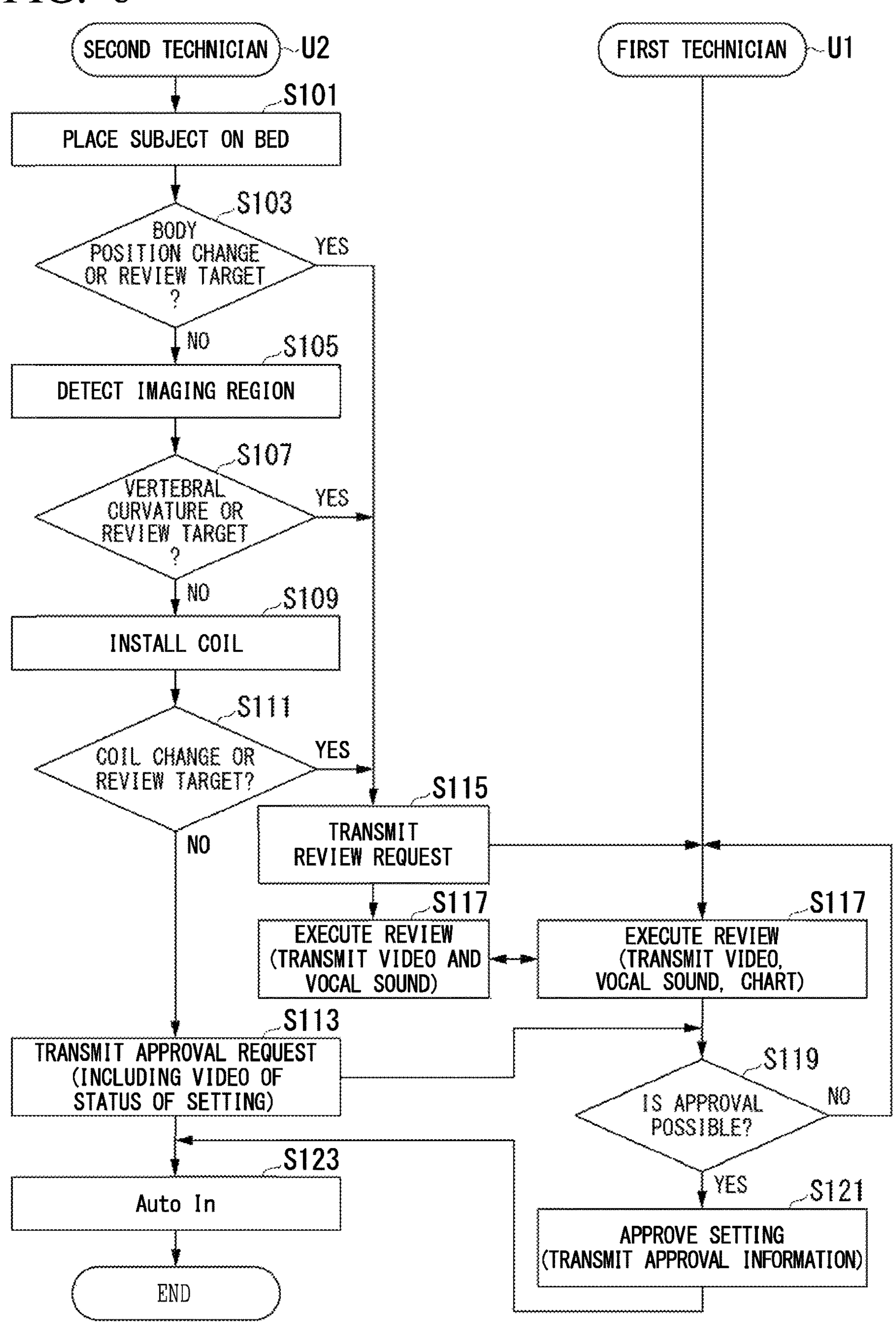
FIG. 6 is a diagram showing a flow of processing executed by a second technician and a first technician.

Next, processing in the medical image diagnostic system 1 will be described. Prior to description of processing in the medical image diagnostic system 1, a flow of processing executed by the first technician U1 and the second technician U2 during an examination will be described. FIG. 6 is a diagram showing a flow of processing executed by the second technician U2 and the first technician U1.

In setting the MRI apparatus 200, the second technician U2 first places a subject P on the top plate 23 of the bed device 20 (step S101). Subsequently, the second technician U2 checks whether or not the body position of the subject P has changed on the top plate 23 and determines whether or not the subject P is a review target for which a review from the first technician U1 will be requested (step S103).

If it is determined that there is no change in the body position and the subject is not a review target, the second technician U2 identifies the content of an examination and detects an imaging region (step S105). Subsequently, the second technician U2 checks whether or not the subject mounted on the top plate 23 has spinal curvature and determines whether or not the subject is a review target for which a review from the first technician U1 will be requested (step S107).

If it is determined that there is no spinal curve and the subject is not a review target, the second technician U2 installs a coil (RF coil) (step S109). The second technician U2 installs the coil by attaching it to the subject P, for example. Subsequently, the second technician U2 checks whether or not the installation state of the installed coil has been changed, and determines whether or not it is a review target for which a review from the first technician U1 will be requested (step S111).

If it is determined that there is no change in the installation state of the coil and it is not a review target, the second technician U2 transmits an approval request for approval of setting to the first technician U1 (step S113). At the time of transmitting the approval request, status information is included in the approval request and transmitted. The first technician U1 determines whether or not setting can be approved by viewing the status information. The second technician U2 waits until setting is approved by the first technician U1.

If it is determined in step S103 that there is a change in the body position or the subject is a review target, the second technician U2 transmits a review request to the first technician U1 (step S115). Similarly, if it is determined in step S107 that there is a spinal curve or the subject is a review target, the second technician U2 transmits a review request to the first technician U1 (step S115). If it is determined in step S111 that there is a change in the installation state of the coil or the coil is a review target, the second technician U2 transmits a review request to the first technician U1 (step S115).

When the second technician U2 transmits the review request, the first technician U1 executes a review together with the second technician U2 (step S117). While the review is executed, in the review terminal 100, the display control function 142 causes the display 130 to display an image according to status information transmitted from the MRI apparatus 200, and the review function 143 generates advice information and transmits the advice information to the MRI apparatus 200.

On the other hand, in the MRI apparatus 200, the transmission function 55 generates status information and transmits the status information to the review terminal 100, and the transmission function 55 transmits advice information transmitted by the review terminal 100 to the second technician U2. As a result of the review, the first technician U1 finally operates an approval switch SW31 (FIG. 10) to approve setting, thereby completing setting of the MRI apparatus 200.

Therefore, the first technician U1 determines whether or not setting can be approved (step S119). Even when the second technician U2 has transmitted an approval request in step S113, the first technician U1 determines whether or not setting can be approved (step S119).

If it is determined that setting cannot be approved, the first technician U1 returns processing to step S117 and performs a review together with the second technician U2. Thereafter, the first technician U1 repeatedly performs reviews with the second technician U2 until it is determined that setting can be approved (step S117).

If it is determined in step S119 that setting can be approved, the first technician U1 approves setting and transmits approval information (step S121). The second technician U2 who has received the approval information makes sure of AutoIn being executed in the MRI apparatus 200 (step S123). Thereafter, the examination in the MRI apparatus 200 is started.

Figure 7:
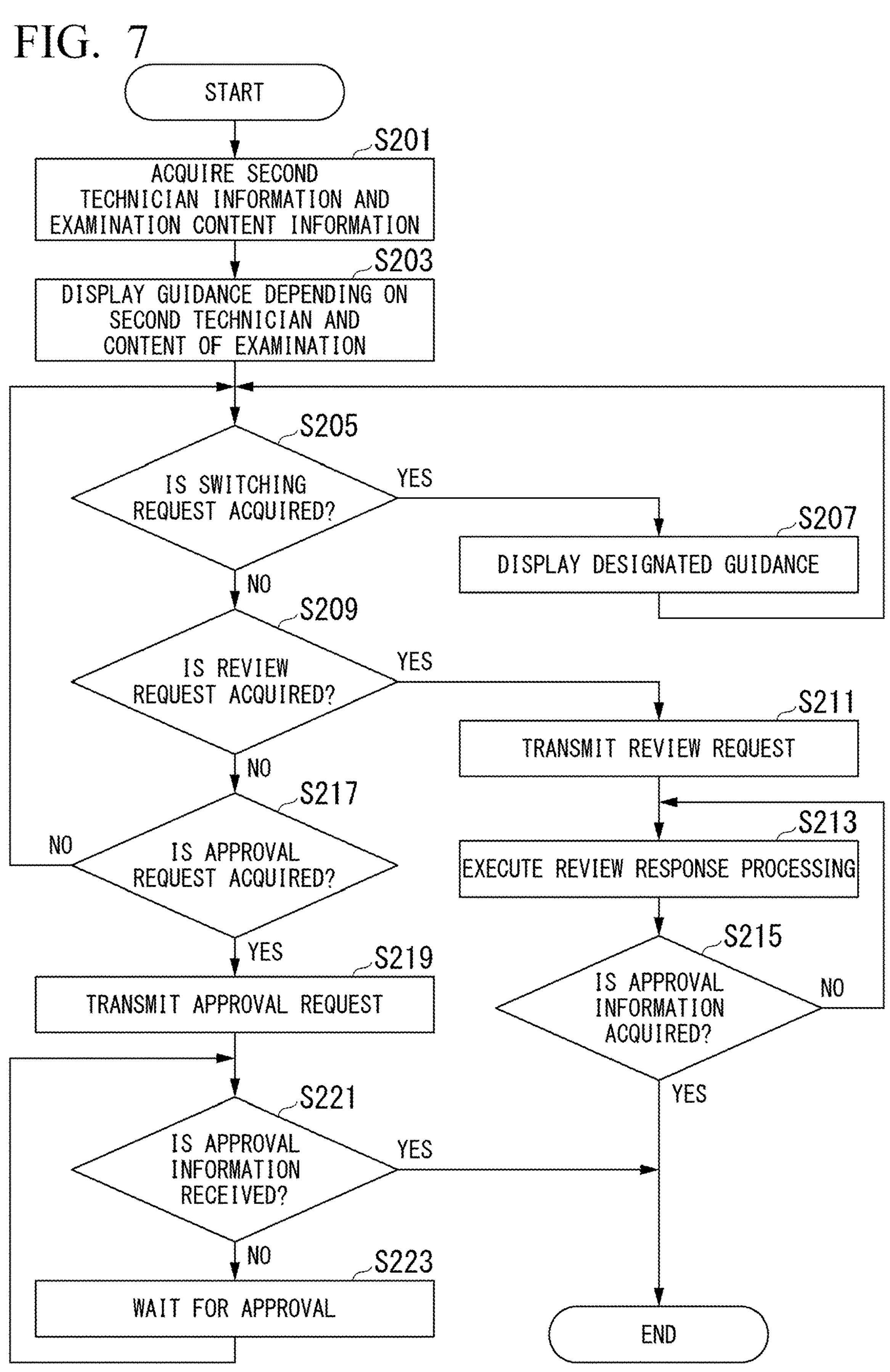
FIG. 7 is a flowchart showing an example of processing of the MRI apparatus.

Next, processing of the MRI apparatus 200 while the first technician U1 and the second technician U2 execute processing will be described. FIG. 7 is a flowchart showing an example of processing in the MRI apparatus 200. In the MRI apparatus 200, first, the acquisition function 51 acquires second technician information and examination content information output from the input interface 43 (step S201).

Subsequently, the provision function 52 reads a guidance designation table corresponding to the name of a second technician U2 included in the second technician information from the memory 41 and provides guidance according to the content of an examination included in the examination content information to the second technician U2 (step S203). The guidance is provided, for example, by displaying the guidance on the display 42 or outputting the guidance from the speaker 63.

Figure 8:
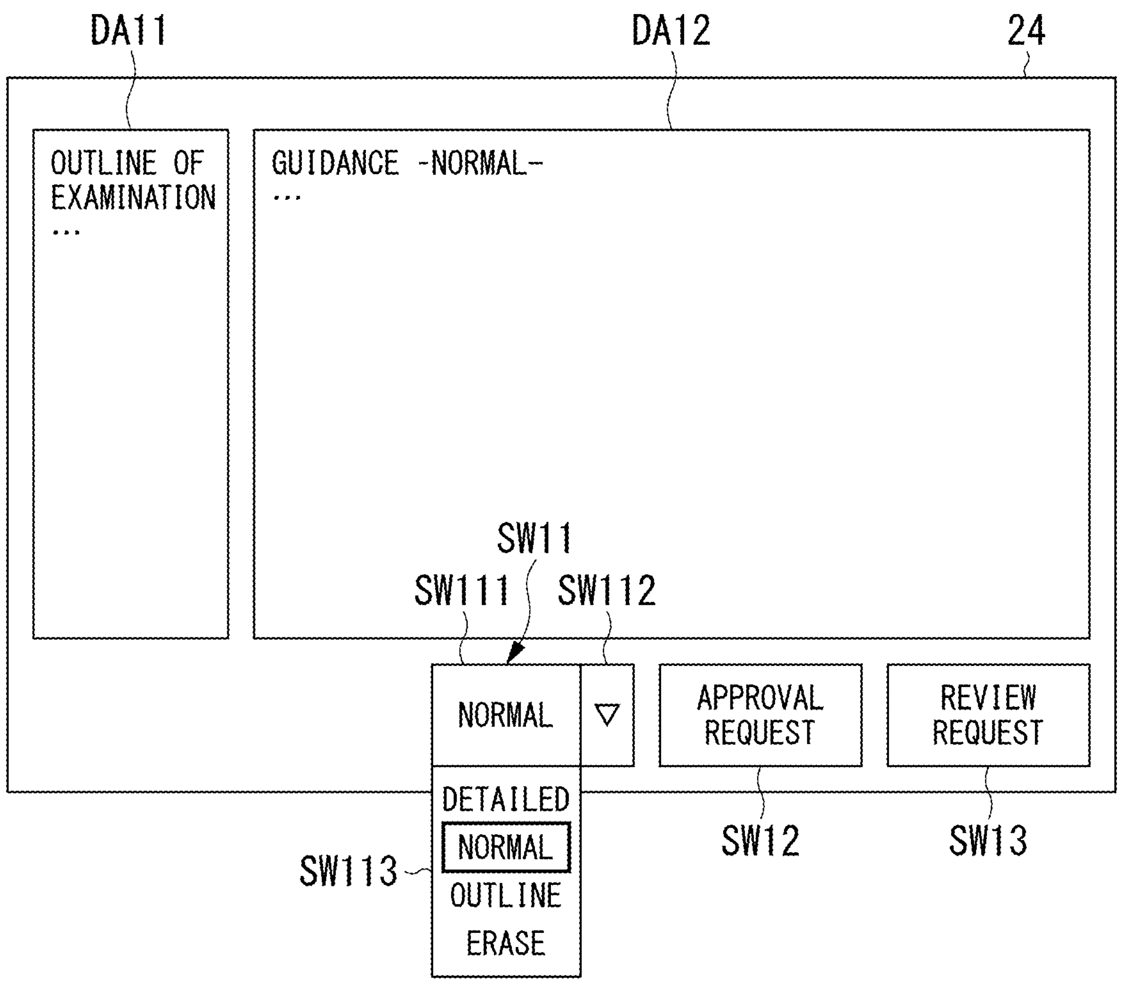
FIG. 8 is a diagram showing an example of a display screen of a display of the MRI apparatus.

Here, an example of content displayed on the display 42 of the MRI apparatus 200 on which guidance is displayed will be described. FIG. 8 is a diagram showing an example of a display screen of the display 42 of the MRI apparatus 200. When the second technician U2 executes setting, for example, the display 42 displays an examination outline display area DA11 that shows the outline of the examination and a guidance display area DA12 that shows the content of the guidance. In the examination outline display area DA11, for example, information such as a patient ID assigned to each patient (subject), a study ID, a patient name, an imaging region, an RF coil and a connection port is displayed.

Images or videos may be displayed in the examination outline display area DA11 and the guidance display area DA12. Images and videos displayed in the examination outline display area DA11 and the guidance display area DA12 may include line drawings and photographs, or text.

The display 42 is further provided with a changeover switch SW11, an approval request switch SW12, and a review request switch SW13. The changeover switch SW11 is, for example, a GUI switch that includes a drop-down menu. The changeover switch SW11 includes, for example, an item display part SW111 in which guidance items displayed in the guidance display area DA12 are displayed, a selection button SW112 set on the right side of the item display part, and a drop-down menu SW113.

While the second technician U2 executes setting of the MRI apparatus 200, for example, the item display part SW111 and the selection button SW112 are displayed on the display 42, and the drop-down menu SW113 is not displayed. When the selection button SW112 is operated in this state, the drop-down menu SW113 is displayed below the item display part SW111. The drop-down menu SW113 displays guidance type items such as "detailed," "normal," and "outline," and "erase." By performing an operation of designating one of the items included in the drop-down menu SW113, guidance with the designated content is displayed in the guidance display area DA12.

The approval request switch SW12 is a GUI switch for requesting transmission of an approval request to the review terminal 100. For example, when the second technician U2 operates the approval request switch SW12, the transmission function 55 transmits an approval request to the review terminal 100.

The review request switch SW13 is a GUI switch for requesting transmission of a review request to the review terminal 100. For example, when the second technician U2 operates the review request switch SW13, the review request function 54 transmits a review request to the review terminal 100.

Referring back to FIG. 6, the switching function 53 determines whether or not a switching request has been acquired by the acquisition function 51 (step S205). If it is determined that a switching request has been acquired, the switching function 53 provides guidance corresponding to the acquired switching request to the second technician U2 (step S207) and returns processing to step S205.

If the switching function 53 determines that a switching request has not been acquired, the review request function 54 determines whether or not a review request has been acquired by the acquisition function 51 (step S209). If it is determined that a review request has been acquired, the review request function 54 transmits the acquired review request to the review terminal 100 using the communication interface 110 (step S211).

By transmitting a review request to the review terminal 100, a review between the first technician U1 and the second technician U2 is started. The transmission function 55 executes review response processing necessary for the review (step S213). As the content of review response processing, the transmission function 55 generates status information including a video captured by the optical camera 61 and sound collected by the microphone 62, and transmits the status information to the review terminal 100.

On the other hand, the transmission function 55 transmits advice information transmitted by the review terminal 100 and received and output by the communication interface 44 to the second technician U2. The review response processing is performed by repeating generation and transmission of status information and reception and transmission of advice information.

Figure 9:
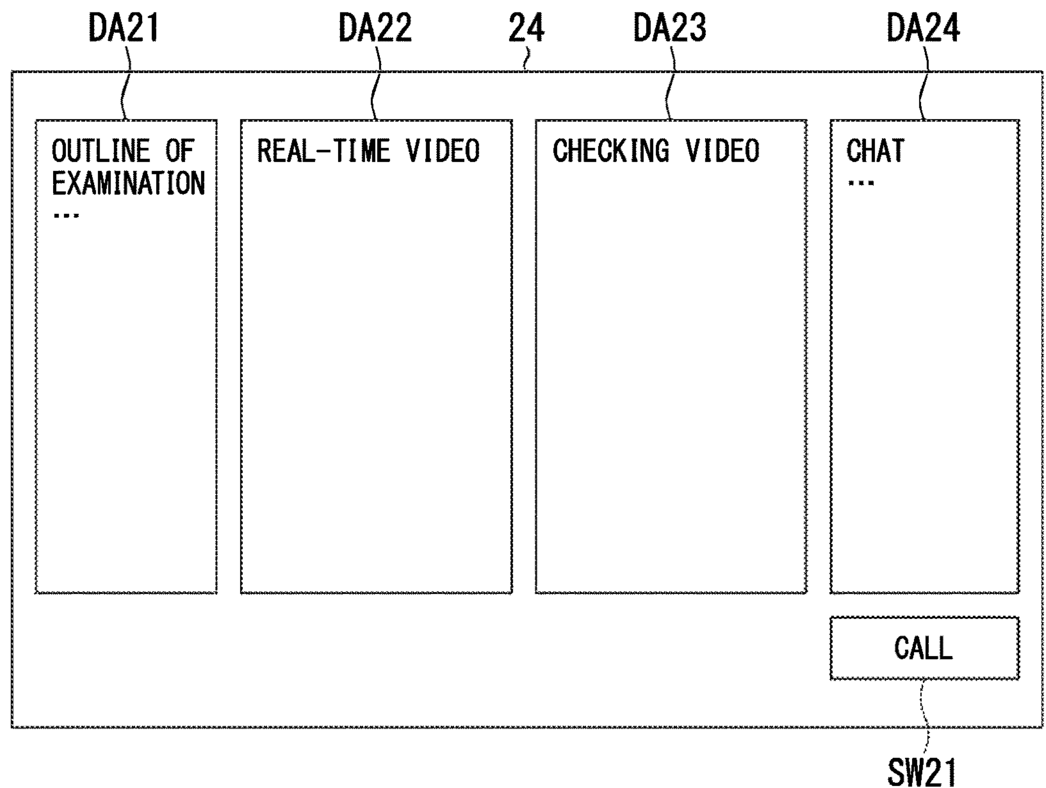
FIG. 9 is a diagram showing an example of a display screen of the display of the MRI apparatus.

Here, an example of display content on the display 42 of the MRI apparatus 200 and the display 130 of the review terminal 100 on which the content of a review and the like are displayed by review response processing will be described. First, display content on the display 42 of the MRI apparatus 200 will be described. FIG. 9 is a diagram showing an example of a display screen of the display 42 of the MRI apparatus 200.

When review response processing is executed, for example, the display 42 displays an examination outline display area DA21, a real-time video display area DA22, a checking video display area DA23, and a chat display area DA24. In the examination outline display area DA21, the outline of an examination similar to the examination outline display area DA11 in FIG. 8 is displayed.

For example, a real-time video captured by the optical camera 61 is displayed in the real-time video display area DA22. A real-time video may be an actual real-time video, or a video obtained by adding a delay of several seconds to a real-time video. A real-time video may be a video obtained by processing a video captured by the optical camera 61 or by adding other images such as figures or characters to a video captured by the optical camera 61. It may also be possible to capture a snapshot from a video displayed in the real-time video display area DA22.

For example, an assistance video (assistance image) for assisting the content of advice given by the first technician U1, and the like are displayed in the checking video display area DA23. In the checking video display area DA23, for example, a snapshot captured when the top plate 23 of the bed device 20 is raised to its uppermost position may be displayed by default, or a snapshot may be captured manually. Further, other images such as figures and characters may also be added to the video in the checking video display area DA23.

In the chat display area DA24, text information included in an inquiry made by the second technician U2 to the first technician U1, advice information given by the first technician U1, and the like are displayed. Images common to images displayed on the display 130 of the review terminal 100 may be displayed in some or all of the real-time video display area DA22, the checking video display area DA23, and the chat display area DA24.

Furthermore, a call switch SW21 is displayed on the display 42. The call switch SW21 is used, for example, when the second technician U2 calls the first technician U1. The first technician U1 may stop reviewing and leave the review terminal 100 in a case where ongoing review response processing takes a long time, a case where a situation requiring a review has ended in setting, and the like. Under such circumstances, when the second technician U2 further requests a review from the first technician U1, the first technician U1 is called through the review terminal 100 by operating the call switch SW21.

Figure 10:
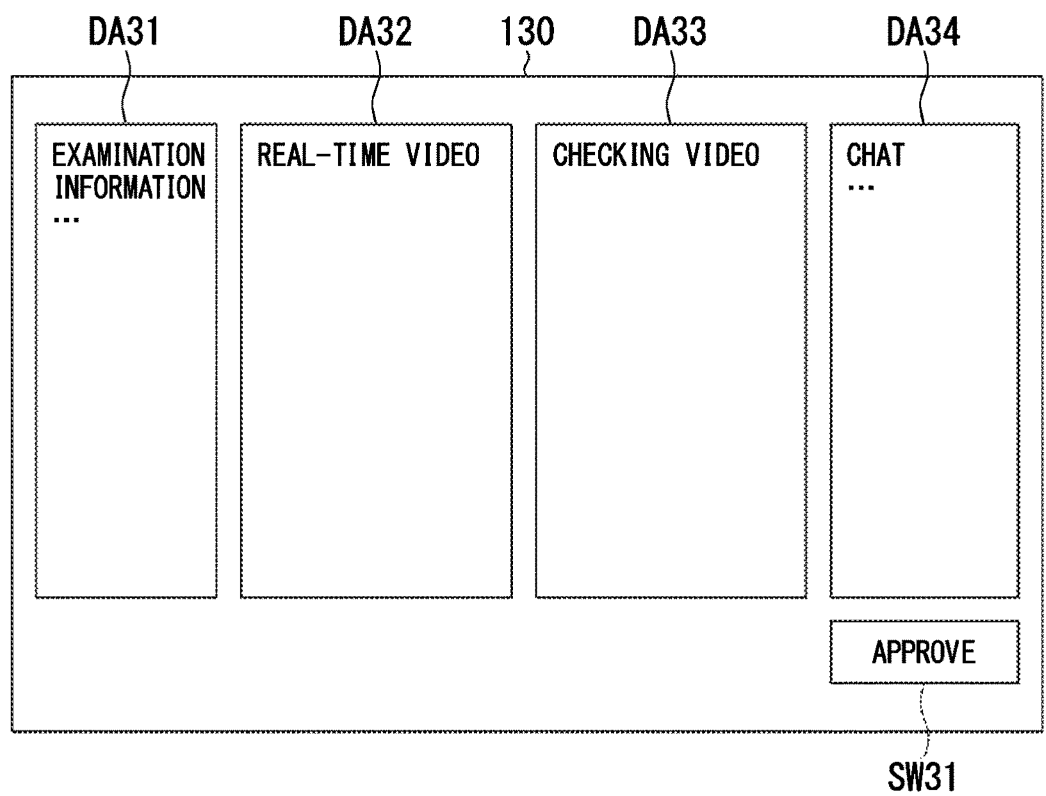
FIG. 10 is a diagram showing an example of a display screen of a display of the review terminal.

Next, display content on the display 42 of the MRI apparatus 200 will be described. FIG. 10 is a diagram showing an example of a display screen of the display 130 of the review terminal 100. When review response processing is executed, for example, the display 130 displays the examination outline display area DA31, the real-time video display area DA32, the checking video display area DA33, and the chat display area DA34. The outline of an examination is displayed in the examination outline display area DA21.

Images common to images displayed in the real-time video display area DA22, the checking video display area DA23, the chat display area DA24 of the display 42 in the MRI apparatus 200 are displayed in the real-time video display area DA32, the checking video display area DA33, and the chat display area DA34 of the display 13 in the review terminal 100.

Furthermore, an approval switch SW31 is set on the display 130. The approval switch SW31 is a GUI switch for approving setting. For example, when the first technician U1 operates the approval switch SW31, the approval function 144 transmits approval information to the MRI apparatus 200.

After the review response processing is executed, the starting function 56 determines whether or not an approval information transmitted by the review terminal 100 has been acquired by the acquisition function 51 (step S215). If it is determined that the approval information has not been acquired, the starting function 56 returns processing to step S213, and the transmission function 55 continues the review response processing. If it is determined that the approval information has been acquired, the MRI apparatus 200 ends processing shown in FIG. 7.

If it is determined in step S209 that the review request has not been acquired, the transmission function 55 determines whether or not an approval request has been acquired by the acquisition function 51 (step S217). If it is determined that the approval request has not been acquired, the transmission function 55 returns processing to step S205. If it is determined that the approval request has been acquired, the transmission function 55 transmits the approval request to the review terminal 100 (step S219).

Subsequently, the starting function 56 determines whether or not approval information transmitted by the review terminal 100 has been acquired by the acquisition function 51 (step S221). If it is determined that the approval information has not been acquired, the starting function 56 waits for approval until the approval information is acquired (step S223). If the starting function 56 determines that the approval information has been acquired, the MRI apparatus 200 ends processing shown in FIG. 7.

The medical image diagnostic system 1 of the embodiment provides setting information set depending on the skill of the second technician U2 to the second technician U2 when the second technician U2 executes setting in the MRI apparatus 200. Therefore, when the second technician U2 sets the MRI apparatus 200, appropriate support can be provided.

In addition, in the medical image diagnostic system 1 of the embodiment, in a case where a review from the first technician U1 is required or at the request from the second technician U2 with respect to the content of setting, a review is performed between the first technician U1 and the second technician U2. Therefore, if the second technician U2 has a low skill level, for example, setting can be performed under the guidance based on the experience of the first technician U1. Furthermore, even if the second technician U2 has a high skill level, advice can be obtained from the first technician U1 who has the same skill level or even higher skill level in a case where the second technician U2 is confused about setting, or the like. Therefore, it is possible to provide appropriate support to the second technician U2 having any skill level.

Furthermore, an imaging plan in the MRI apparatus 200 may change depending on setting. Therefore, in a case where the first technician U1 images the subject P remotely from the MRI apparatus 200, for example, it is necessary to present the status of setting to the first technician U1. In this regard, status information is transmitted from the MRI apparatus 200 to the review terminal 100 in the medical image diagnostic system 1 of the embodiment. Therefore, even in a situation in which the first technician U1 is in charge of the imaging operation using the remote review terminal 100, it is possible to realize an imaging plan in consideration of the status of setting for the subject P.

According to at least one embodiment described above, the medical image diagnostic apparatus includes processing circuitry. The processing circuitry acquires skill information regarding a skill of a user who sets the medical image diagnostic apparatus, and provides setting information for the medical image diagnostic apparatus according to the skill of the user based on the acquired skill information to the user. Accordingly, it is possible to perform appropriate support for the user.

Although several embodiments have been described, these embodiments are presented as examples and are not intended to limit the scope of the invention. These embodiments can be implemented in various other forms, and various omissions, substitutions, and modifications can be made without departing from the spirit of the invention. These embodiments and modifications thereof are included in the scope and spirit of the invention, as well as the scope of the invention described in the claims and equivalents thereof.

What is claimed is:

1. A medical image diagnostic apparatus, comprising:

processing circuitry configured to:

acquire skill information regarding a skill of a user who sets the medical image diagnostic apparatus; and provide setting information for the medical image diagnostic apparatus according to the skill of the user based on the acquired skill information to the user, wherein the setting information is information related to an operation of the medical image diagnostic apparatus for a purpose of acquiring a medical image, or a condition under which the medical image is acquired using the medical image diagnostic apparatus, wherein the medical image diagnostic apparatus further comprises a memory configured to store information associated with type of examination performed by the medical image diagnostic apparatus, the skill information, and the setting information, and wherein the processing circuitry is further configured to perform a diagnosis of the medical image according to the operation or the condition defined by the setting information, based on an operation of the user.

2. The medical image diagnostic apparatus according to claim 1, wherein a plurality of levels depending on the skill are set as the setting information, and the processing circuitry is further configured to provide the setting information corresponding to any one of the plurality of levels to the user.

3. The medical image diagnostic apparatus according to claim 1, wherein the processing circuitry is further configured to set the setting information for each of a plurality of users.

4. The medical image diagnostic apparatus according to claim 2, wherein the processing circuitry is further configured to set the setting information depending on a use form of the medical image diagnostic apparatus.

5. The medical image diagnostic apparatus according to claim 1, wherein the processing circuitry is further configured to switch the provided setting information in response to an instruction from the user while the setting information is being provided.

6. The medical image diagnostic apparatus according to claim 1, wherein the setting information includes guidance set depending on the skill of the user and advice information regarding setting of the medical image diagnostic apparatus proposed by another user different from the user.

7. The medical image diagnostic apparatus according to claim 6, wherein the advice information includes at least either image information or verbal information.

8. The medical image diagnostic apparatus according to claim 7, wherein the processing circuitry is further configured to provide the verbal information through text or vocal sound.

9. The medical image diagnostic apparatus according to claim 1, wherein the processing circuitry is further configured to transmit a status of setting being performed in the medical image diagnostic apparatus to another user.

10. The medical image diagnostic apparatus according to claim 9, wherein the processing circuitry is further configured to transmit at least one of an image or a sound with respect to the status of setting to the other user.

11. The medical image diagnostic apparatus according to claim 6, wherein the processing circuitry is further configured to request a review for obtaining the advice information from the other user.

12. A computer-readable non-transitory storage medium storing a program to be executed by a computer of a medical image diagnostic apparatus, the program causing the computer to perform:

acquiring skill information regarding a skill of a user who sets the medical image diagnostic apparatus; and providing setting information for the medical image diagnostic apparatus according to the skill of the user based on the acquired skill information to the user, wherein the setting information is information related to an operation of the medical image diagnostic apparatus for a purpose of acquiring a medical image, or a condition under which the medical image is acquired using the medical image diagnostic apparatus, wherein the medical image diagnostic apparatus comprises a memory configured to store information associated with type of examination performed by the medical image diagnostic apparatus, the skill information, and the setting information, and the program further causes the computer to perform a diagnosis of the medical image according to the operation or the condition defined by the setting information, based on an operation of the user.

* * * * *